(12) United States Patent
Kloppenburg et al.

(10) Patent No.: US 10,203,319 B2
(45) Date of Patent: Feb. 12, 2019

(54) DETERMINATION OF THE DEGREE OF BRANCHING

(71) Applicant: ARLANXEO Deutschland GmbH, Dormagen (DE)

(72) Inventors: Heike Kloppenburg, Duesseldorf (DE); Alicia Le-Sattler, Bochum (DE)

(73) Assignee: ARLANXEO DEUTSCHLAND GMBH, Dormagen (DE)

(*) Notice: Subject to any disclaimer, the term of this patent is extended or adjusted under 35 U.S.C. 154(b) by 164 days.

(21) Appl. No.: 15/028,550

(22) PCT Filed: Oct. 9, 2014

(86) PCT No.: PCT/EP2014/071685
§ 371 (c)(1),
(2) Date: Apr. 11, 2016

(87) PCT Pub. No.: WO2015/055511
PCT Pub. Date: Apr. 23, 2015

(65) Prior Publication Data
US 2016/0231305 A1    Aug. 11, 2016

(30) Foreign Application Priority Data
Oct. 16, 2013 (EP) .................................. 13188978

(51) Int. Cl.
| | | |
|---|---|---|
| G01N 33/00 | (2006.01) | |
| G01N 33/44 | (2006.01) | |
| C08C 19/20 | (2006.01) | |
| C08L 9/00 | (2006.01) | |
| C08C 19/22 | (2006.01) | |
| C08C 19/25 | (2006.01) | |
| G01N 11/16 | (2006.01) | |

(52) U.S. Cl.
CPC ........... *G01N 33/442* (2013.01); *C08C 19/20* (2013.01); *C08C 19/22* (2013.01); *C08C 19/25* (2013.01); *C08L 9/00* (2013.01); *G01N 11/162* (2013.01)

(58) Field of Classification Search
CPC .................................................... G01N 33/442
USPC ......................................................... 436/85
See application file for complete search history.

(56) References Cited

U.S. PATENT DOCUMENTS

| | | | |
|---|---|---|---|
| 3,374,191 A | 3/1968 | Nutzel | |
| 4,260,707 A | 4/1981 | Sylvester et al. | |
| 5,914,377 A | 6/1999 | Sylvester et al. | |
| 6,417,285 B2 | 7/2002 | Giebeler et al. | |
| 8,283,401 B2 | 10/2012 | Murakami et al. | |
| 8,394,883 B2 | 3/2013 | Viola et al. | |
| 2001/0025071 A1 | 9/2001 | Fruh et al. | |
| 2008/0162055 A1* | 7/2008 | Wrana .................... | G01N 11/14 702/23 |
| 2009/0156751 A1* | 6/2009 | Kwag .................... | C08C 19/20 525/332.4 |
| 2011/0136956 A1* | 6/2011 | Kwag .................... | C08C 19/20 524/423 |
| 2016/0083531 A1 | 3/2016 | Steinhauser et al. | |

FOREIGN PATENT DOCUMENTS

| | | |
|---|---|---|
| CN | 103012842 A | 4/2013 |
| EP | 0011184 A1 | 5/1980 |
| JP | 9003120 A2 | 1/1997 |
| JP | 2000186154 A2 | 7/2000 |

OTHER PUBLICATIONS

William W. Graessley and Henry M. Mittelhauser "Intrinsic Viscosity of Polydisperse Branched Polymers" Journal of Polymer Science: Part A-2 vol. 5, 431-454 (1967) (Year: 1967).*
European Search Report from European Application No. 13188978, dated Mar. 20, 2014, two pages.

* cited by examiner

*Primary Examiner* — Christine T Mui
*Assistant Examiner* — Emily R. Berkeley
(74) *Attorney, Agent, or Firm* — Norris McLaughlin, P.A.

(57) ABSTRACT

The invention relates to a process for determining the degree of branching of modified polymers wherein the polymers are modified in the sense that their degree of branching after polymerization was increased once more, wherein the modified polymers are treated with a polar transformation mixture comprising a compound of general formula (I)

$$R^1{-}S{-}S{-}R^1 \qquad (I)$$

wherein the Mooney viscosity (ML 1+4 at 100° C.) of the polymers is determined before and after the treatment with the polar transformation mixture and the degree of branching is determined.

18 Claims, No Drawings

DETERMINATION OF THE DEGREE OF BRANCHING

The invention relates to a process for determining the degree of branching of modified polymers wherein the polymers are modified in the sense that their degree of branching after polymerization was increased.

Polybutadienes are used as important constituents of rubber mixtures in the tyre industry in order to achieve an improvement in final properties, for instance a reduction in rolling resistance and in abrasion value. A further field of use is in golf-ball cores or shoe soles, the primary concern in this case being a high rebound resilience.

Polybutadienes having a high fraction of cis-1,4 units have now been manufactured on a large industrial scale—and used for the production of tyres and other rubber products and also for impact modification of polystyrene—for quite some time.

The high fractions of cis-1,4 units are currently achieved by using almost exclusively catalysts based on compounds of the rare earth metals, as described in EP-A 1 0 011 184 and EP-B-A1 0 007 027 for example.

It is known from the prior art that specifically neodymium-catalysed polybutadienes within the group of high-cis polybutadienes have particularly advantageous properties with regard to rolling resistance, abrasion value and rebound resilience. The catalyst systems used play an important part in the production of polybutadienes.

The industrially employed neodymium catalyst, for example, is a Ziegler-Natta system, which is formed from a plurality of catalyst components. Catalyst formation involves the formation of mostly different catalytic sites, resulting in an at least bimodal molar mass distribution in the polymer. In the Ziegler-Natta catalyst system, the familiar 3 catalyst components, usually consisting of a neodymium source, a chloride source and an organoaluminum compound, are mixed in various ways under defined temperature conditions to ready the catalyst system for the polymerization with or without aging.

The prior art discloses several processes for preparing Ziegler-Natta catalyst systems used in the production of polybutadienes.

It is known that commercially produced polymers have a statistical molar mass distribution the width of which is influenced by the way the catalyst was produced.

Raising the molecular weight of elastomeric unsaturated diene polymers is important for various reasons. It first of all makes it possible to produce low molecular weight parent polymers, which has the immense advantage in relation to the solution polymerization techniques typically employed of entailing lower viscosities in the "cement" (the solution of the polymer in the organic solvent medium used in the polymerization) and of permitting operation at higher solids contents in the "cement", since superior heat transfer is achieved. It is further possible to reduce the cold flow of such diene polymers, thus increasing their capability for oil-extension.

It is further known that polydienes having low cold flow are obtainable by treating the diene polymers with disulphur dichloride, sulphur dichloride, thionyl chloride, disulphur dibromide or thionyl bromide after the polymerization (DE-B 12 60 794).

The expression "step increase in Mooney viscosity" and similar expressions, for instance "Mooney jumped" or "Mooney jump", refer to techniques to significantly enhance the Mooney viscosity (ML 1+4 at 100° C.) of the polymers after the polymerization and/or the degree of branching. The polymer is typically modified with $S_2Cl_1$ in order to branch the polymer via sulphur bridge bonding in accordance with the following schematic reaction equation:

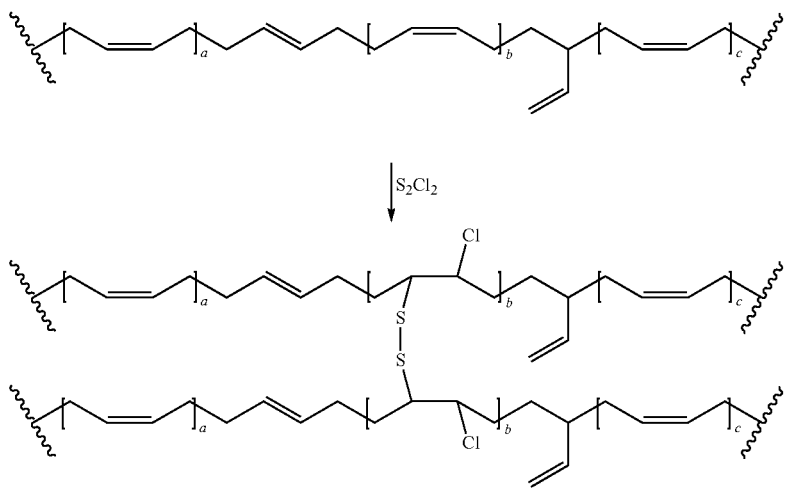

The degree of branching or the Mooney viscosity (ML 1+4 at 100° C.) is accordingly increased. The reaction scheme shown above describes the "Mooney jump" for a high-cis polybutadiene by way of example in that this reaction can also be performed on any other diene-containing polymers.

The modification typically utilizes sulphur halides, preferably disulphur dichloride, sulphur chloride, sulphur bromide, sulphur dichloride, thionyl chloride, disulphur dibromide or thionyl bromide.

Yet no method is known to date for subsequently determining this step increase in the Mooney viscosity and/or the increase in the degree of branching with "Mooney jumped" polymers, which are now in the form of a solid material. Customary measurement of the Mooney viscosity (ML 1+4 at 100° C.) on a solid polymer material merely reveals the final Mooney viscosity, i.e. the Mooney viscosity (ML 1+4 at 100° C.) after modification with sulphur chlorides.

The original Mooney viscosity (ML 1+4 at 100° C.), i.e. the Mooney viscosity (ML 1+4 at 100° C.) after polymerization, is not known for a modified solid polymer material.

The problem addressed by the present invention is therefore that of providing a process for determining the degree of branching of polymers modified in the sense that their degree of branching after polymerization was increased again.

The problem is solved by a process for determining the degree of branching of modified polymers wherein the polymers are modified in the sense that their degree of branching after polymerization was increased once more, wherein the modified polymers are treated with a transformation mixture comprising a compound of general formula (I)

$$R^1\text{—}S\text{—}S\text{—}R^1 \qquad (I)$$

where
R$^1$ in either occurrence is the same or different and is selected from a group of
moieties of formula (II)

$$C_6(R^2)_5\text{—}(C\!\!=\!\!O)\text{—}N(R^3)\text{—}C_6(R^2)_4\text{—} \qquad (II)$$

where R$^2$ and R$^3$ in each occurrence is the same or different and they each represent a hydrogen radical, a linear or branched alkyl radical of 1 to 16 carbon atoms, preferably 1 to 8 carbon atoms, a phenyl radical or a cycloalkyl radical of 5 to 8 carbon atoms;
a moiety of formula (III)

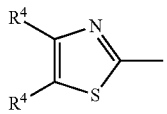
(III)

where R$^4$ in either occurrence is the same or different and represents a hydrogen, halogen, nitro or hydroxyl radical, a linear or branched alkyl radical of 1 to 12 carbon atoms, preferably 1 to 8 carbon atoms, a linear or branched alkoxy radical of 1 to 12 carbon atoms, preferably 1 to 8 carbon atoms, a phenyl radical or a cycloalkyl radical of 5 to 8 carbon atoms or the R$^4$'s combine to form the moiety of formula (IV);

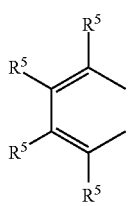
(IV)

where R$^5$ in each occurrence is the same or different and represents a hydrogen or hydroxyl radical, a linear or branched alkyl radical of 1 to 12 carbon atoms, preferably of 1 to 8 carbon atoms, a linear or branched alkoxy radical of 1 to 12 carbon atoms, preferably of 1 to 8 carbon atoms, a phenyl radical or a cycloalkyl radical of 5 to 8 carbon atoms;
a moiety of formula (V)

$$(R^6O)_3Si\text{—}(CH_2)_n\text{—}(Y)_m\text{—} \qquad (V)$$

where
n is an integer from 1 to 12, preferably from 1 to 6;
m is from 0 to 4, preferably from 0 to 2;
R$^6$ in each occurrence is the same or different and represents a linear or branched alkyl radical of 1 to 16 carbon atoms, preferably 1 to 8 carbon atoms, a phenyl radical or a cycloalkyl radical of 5 to 8 carbon atoms;
Y represents sulphur, a moiety of formula VIa, VIb, VIc, VId or VIe

(VIa)

(VIb)

(VIc)

(VId)

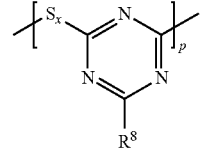
(VIe)

where
x is an integer from 1 to 8, preferably from 2 to 6;
p is an integer from 1 to 12, preferably from 1 to 6;
R$^8$ in each occurrence is the same or different and represents a linear or branched alkyl radical of 1 to 16 carbon atoms, preferably 1 to 8 carbon atoms, an alkoxy radical of 1 to 16 carbon atoms, preferably 1 to 8 carbon atoms, a phenyl radical or a phenoxy radical;
a moiety of formula (VII)

$$(R^9)_2N\text{—}(C\!\!=\!\!Z)\text{—} \qquad (VII)$$

where
Z represents sulphur or oxygen,
R$^9$ in either occurrence is the same or different and represents a linear or branched alkyl radical of 1 to 16 carbon atoms, preferably 1 to 8 carbon atoms, a phenyl radical or a cycloalkyl radical of 5 to 8 carbon atoms;
a moiety of formula (VIII)

$$R^{10}\text{—}O\text{—}C(\!\!=\!\!S)\text{—} \qquad (VIII)$$

where
R$^{10}$ in either occurrence is the same or different and represents a linear or branched alkyl radical of 1 to 16 carbon atoms, preferably 1 to 8 carbon atoms, a phenyl radical or a cycloalkyl radical of 5 to 8 carbon atoms,
wherein the Mooney viscosity (ML 1+4 at 100° C.) of the modified polymers is determined before and after the treatment with the transformation mixture and the degree of branching is determined by calculation.

The degree of branching is determined as follows: The Mooney viscosities (ML 1+4 at 100° C.) of the modified polymers are measured before and after the treatment with the transformation mixture and determined according to equation (I) below:

degree of branching in %=(K−L)/L*100 (5)

K=Mooney viscosity (ML 1+4 at 100° C.) of the polymers before treatment with the transformation mixture
L=Mooney viscosity (ML 1+4 at 100° C.) of the polymers after treatment with the transformation mixture Surprisingly, the process of the present invention was found to be capable of determining the original Mooney viscosity of the polymers. Original Mooney viscosity (ML 1+4 at 100° C.) here refers to the Mooney viscosity which was determined on the polymer, typically by the method of ASTM D1646-00, after polymerization.

In one embodiment of the invention, A process for determining the degree of branching of modified diene polymers wherein the degree of crosslinking/branching of the modified diene polymers has been increased, comprising: determining the Mooney viscosity (ML 1+4 at 100° C.) of the modified diene polymers, treating the modified diene polymers with a transformation mixture, thereby forming further modified diene polymers, wherein the transformation mixture comprises a compound of general formula (I)

$$R^1-S-S-R^1 \quad (I)$$

where
$R^1$ in either occurrence is the same or different and is selected from a group of
moieties of formula (II)

$$C_6(R^2)_5-(C=O)-N(R^3)-C_6(R^2)_4- \quad (II)$$

where $R^2$ and $R^3$ in each occurrence is the same or different and they each represent a hydrogen radical, a linear or branched alkyl radical of 1 to 16 carbon atoms, preferably 1 to 8 carbon atoms, a phenyl radical, a cycloalkyl radical of 5 to 8 carbon atoms;
a moiety of formula (III)

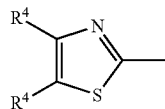

(III)

where $R^4$ in either occurrence is the same or different and represents a hydrogen, halogen, nitro or hydroxyl radical, a linear or branched alkyl radical of 1 to 12 carbon atoms, preferably 1 to 8 carbon atoms, a linear or branched alkoxy radical of 1 to 12 carbon atoms, preferably 1 to 8 carbon atoms, a phenyl radical, a cycloalkyl radical of 5 to 8 carbon atoms or the $R^4$'s combine to form the moiety of formula (IV);

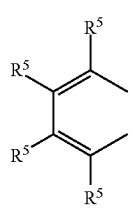

(IV)

where $R^5$ in each occurrence is the same or different and represents a hydrogen or hydroxyl radical, a linear or branched alkyl radical of 1 to 12 carbon atoms, preferably of 1 to 8 carbon atoms, a linear or branched alkoxy radical of 1 to 12 carbon atoms, preferably of 1 to 8 carbon atoms, a phenyl radical, a cycloalkyl radical of 5 to 8 carbon atoms;
a moiety of formula (V)

$$(R^6O)_3Si-(CH_2)_n-(Y)_m- \quad (V)$$

where
n is an integer from 1 to 12, preferably from 1 to 6;
m is from 0 to 4, preferably from 0 to 2;
$R^6$ in each occurrence is the same or different and represents a linear or branched alkyl radical of 1 to 16 carbon atoms, preferably 1 to 8 carbon atoms, a phenyl radical or a cycloalkyl radical of 5 to 8 carbon atoms;
Y represents sulphur, a moiety of formula VIa, VIb, VIc, VId or VIe

(VIa)

(VIb)

(VIc)

(VId)

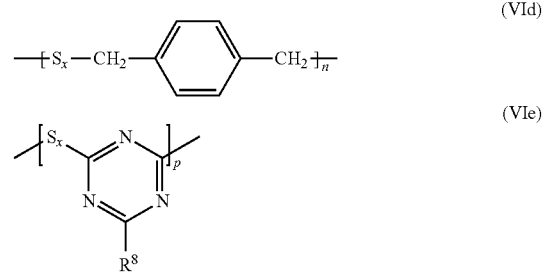

(VIe)

where
x is an integer from 1 to 8, preferably from 2 to 6;
p is an integer from 1 to 12, preferably from 1 to 6;
$R^8$ in each occurrence is the same or different and represents a linear or branched alkyl radical of 1 to 16 carbon atoms, preferably 1 to 8 carbon atoms, an alkoxy radical of 1 to 16 carbon atoms, preferably 1 to 8 carbon atoms, a phenyl radical or a phenoxy radical;
a moiety of formula (VII)

$$(R^9)_2N-(C=Z)- \quad (VII)$$

where
Z represents sulphur or oxygen,
$R^9$ in either occurrence is the same or different and represents a linear or branched alkyl radical of 1 to 16 carbon atoms, preferably 1 to 8 carbon atoms, a phenyl radical or a cycloalkyl radical of 5 to 8 carbon atoms;
a moiety of formula (VIII)

$$R^{10}-O-C(=S)- \quad (VIII)$$

where
$R^{10}$ in either occurrence is the same or different and represents a linear or branched alkyl radical of 1 to 16 carbon atoms, preferably 1 to 8 carbon atoms, a phenyl radical or a cycloalkyl radical of 5 to 8 carbon atoms, after said treating step with the transformation mixture,
determining the Mooney viscosity (ML 1+4 at 100° C.) of the further modified diene polymers, and
determining the degree of branching of the modified diene polymers according to equation (I):

degree of branching in %=$(K-L)/L*100$ where
K is the Mooney viscosity (ML 1+4 at 100° C.) of the modified diene polymers before treating with the transformation mixture and
L is the Mooney viscosity (ML 1+4 at 100° C.) of the further modified diene polymers after treatment with the transformation mixture.

In the process of the present invention, 2,2'-dibenzamidodiphenyl disulphide (DBD)

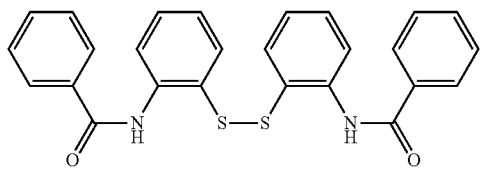 [SMILES: O=C(Nc1ccccc1SSc1ccccc1NC(=O)c1ccccc1)c1ccccc1]

is preferably included in the transformation mixture.

The transformation mixture preferably comprises a compound of formula (IXa)

$(EtO)_3Si-C_3H_6-S_4-C_3H_6-Si(OEt)_3$ (IXa), or a compound of formula (IXb)

$(EtO)_3Si-C_3H_6-S_2-C_3H_6-Si(OEt)_3$ (IXb)

The transformation mixture more preferably comprises tetramethylthiuram disulphide.

The transformation mixture further preferably comprises transition metal salts selected from Fe, Co, Cu, Ni, Mn, Cr, preferably Fe, by way of activator. The Fe salts comprise Fe phthalocyanine or Fe hematoporphyrin.

It is also conceivable for the transformation mixture to comprise pentachlorothiophenol and salts thereof, preferably Zn salts, by way of activator.

Useful activators further include organic peroxides of formula (VIII)

$R^{11}-O-O-R^{12}$, (VIII)

where $R^{11}$ and $R^{12}$ are the same or different and each represent a
hydrogen radical,
a linear or branched alkyl radical of 1 to 16 carbon atoms, preferably 1 to 8 carbon atoms, a phenyl radical or a cycloalkyl radical of 5 to 8 carbon atoms,
a carboxyl radical $R^{13}-(C=O)-$, where $R^{13}$ represents a linear or branched alkyl radical of 1 to 16 carbon atoms, preferably 1 to 8 carbon atoms, a phenyl radical or a cycloalkyl radical of 5 to 8 carbon atoms.

The transformation mixture preferably further comprises waxes and/or fillers to ensure optimum distribution in the polymer.

Waxes used may be, for example, hydrocarbons, such as oils, paraffins and PE waxes, fatty alcohols of 6 to 20 carbon atoms, ketones, carboxylic acids, such as fatty acids and montan acids, oxidized PE wax, metal salts of carboxylic acids, carboxamides and also carboxylic esters, for example esters of ethanol, fatty alcohols, glycerol, ethanediol, pentaerythritol and long-chain carboxylic acids as acid component.

Active or inert fillers may be used. Active fillers used include, for example, hydroxyl-containing oxidic fillers, preferably silica or other hydrophilic pyrogenous or precipitated silicas, in which case mixed oxides with other metal oxides, such as the oxides of Al, of Mg, of Ca, of Ba, of Zn, of Zr or of Ti are possible. Carbon blacks may further be used for example. It is likewise possible to use natural silicates, such as kaolin and other naturally occurring silicas, metal oxides, such as zinc oxide, calcium oxide, magnesium oxide or aluminium oxide, metal carbonates, such as calcium carbonate, magnesium carbonate or zinc carbonate, metal sulphates, such as calcium sulphate or barium sulphate, metal hydroxides, such as aluminium hydroxide or magnesium hydroxide.

The process of the present invention is preferably used for determining the degree of branching of the solid polymer material.

Preferably the polymer is mixed with the transformation mixture under thermal or mechanical input of energy. Any customary mixing assemblies can be used for this, for example a roll, a kneader, a mixer or an extruder.

Any roll may be selected. The ideal choice for analytical proof of concept is a laboratory roll, which is preferably capable of handling polymers from 100 g to 2 kg. Roll diameter is preferably between 5 and 30 cm. Roll nip is chosen such that the milled sheet produced will be homogeneous. Roll nip is preferably between 0.3 and 2 mm, more preferably between 0.4 and 1 mm. Roll speed is chosen such that the operator can work efficiently and the milled sheet can be cut and folded over by hand to improve homogenization. The roll may be operated with or without friction. The amount of transformation mixture used may be between 0.1 and 2 wt % based on the polymer used. Larger amounts of transformation mixture may also be added, but this will not result in any further increase in efficacy.

The roll may be heated by an external temperature-regulating system to different temperatures. Temperatures between 70° C. and 160° C. are preferable and between 80° C. and 120° C. are particularly preferable. The ideal roll temperature is easily determined by preliminary tests. It depends on the heat transfer from the roll to the polymer, which in turn depends on the ratio of the roll surface area to the amount of polymer used, and on the activator used.

Roll temperature is preferably between 90° C. and 120° C. when iron phthalocyanine is used. Without activator in the transformation mixture, higher temperatures are preferably needed, and they are typically between 100° C. and 140° C.

Treatment duration depends on the temperature of the polymer on the roll and on the activator used in the transformation mixture. Treatment time is typically between 1 min and 30 min and may be determined by preliminary tests. An optimum combination of roll temperature and polymer quantity and amount of transformation mixture can ideally reduce the treatment time to the range from 1 to 10 min.

The length of the treatment of the polymer with the transformation mixture is preferably from 1 to 30 min, more preferably from 3 to 15 min.

It is particularly preferable for the transformation mixture to have the following composition:
a) 5 to 100 wt % of one or more compounds of formula (I), preferably 30 to 50 wt %,
b) optionally 0.01 to 5 wt % of activators, preferably 0.3 wt %-1 wt %, at the quantitative expense of compound of formula (I), c) optionally 0.01 to 90 wt % of waxes, preferably 30 wt %-50 wt %, at the quantitative expense of compound of formula (I),
d) optionally 0.01 to 90 wt % of fillers, preferably 10 wt %-30 wt %, at the quantitative expense of compound of formula (I),
based on 100 wt % of transformation mixture.

The transformation mixture used may preferably comprise one or more compounds of formula (I).

The transformation mixture preferably comprises a polar transformation mixture.

The invention further provides for the use of the process according to the invention for determining the degree of branching of modified polymers.

Any type of polymer where the degree of branching was increased subsequently, i.e. after polymerization, can be used.

This comprehends polybutadienes of high 1,4-cis content (>90 wt % of 1,4-cis content based on the polybutadiene) obtained using catalysts based on Ni, Co, Ti or Nd, and also polybutadienes having a vinyl content of 0 to 75 wt % and obtained using Li-based catalysts, polyisoprenes, solution SBR rubbers, optionally modifiable with functional groups, or isobutylene-isoprene copolymers.

The examples which follow are offered by way of further elucidation of the invention.

EXAMPLE 1: DETERMINING A 55% DEGREE OF BRANCHING IN A MODIFIED POLYMER OF LOW MOONEY VISCOSITY

1a) Polymerization:
A dry, nitrogen-inertized 20 L steel autoclave was charged with 8500 g of hexane (dried over molecular sieve), 1300 g of 1,3-butadiene, 25 mmol of a 20% solution of diisobutylaluminium hydride in hexane, 1.44 mmol of a 10% solution of ethylaluminium sesquichloride in hexane, and also 1.44 mmol of a 40% solution of neodymium versatate in hexane. The autoclave contents were heated to 65° C. with stirring and polymerized for 60 min with stirring. The temperature in the reactor was maintained at 70° C. The polymerization was stopped by admixture of 6.5 g of lauric acid (0.5 phr) and stabilized by admixture of 1.3 g of Irganox 1520.

A conversion test sample was taken. Butadiene conversion after the polymerization was found to be 95%.
Original Mooney viscosity (ML 1+4 at 100° C.): 29.8 MU; microstructure: 97.3 wt % of 1,4-cis, 1.8 wt % of 1,4-trans, 0.8 wt % of 1,2-vinyl
1b) Modification:
720 g of polymer solution 1 a) were transferred into a 2 L reactor. The solution was admixed with a solution of 0.187 g of disulphur dichloride (0.2 phr) in 10 mL of hexane at 65° C. for modification. The solution was stirred at 65° C. for a further 30 min. The polymer was precipitated by introduction into 5 kg of ethanol, stabilized with further Irganox 1520 (0.1 phr) and vacuum dried at 70° C.
Final Mooney viscosity (ML 1+4 at 100° C.): 45.6 MU corresponds to K as per equation (I) for computing the degree of branching
Gel content<0.3 wt %
1c) Determination of Degree of Branching
A mixture of 4 g of DBD with 6 g of talcum and 0.08 g of iron phthalocyanine was mixed in a mortar by way of transformation mixture.

70 g of the polymer from 1b) were admixed with 0.44 g of the transformation mixture on a laboratory roll at 120° C. Roll nip was 0.4 mm, roll diameter was 10 cm. Rolling time was 15 min.
Mooney viscosity (ML 1+4 at 100° C.): 29.4 MU corresponds to L as per equation (I) for computing the degree of branching [%]=(K−L)/L*100=(45.6−29.4)/29.4*100=55
Degree of branching: 55%

EXAMPLE 2: DETERMINING A 17% DEGREE OF BRANCHING IN A MODIFIED POLYMER OF LOW MOONEY VISCOSITY

2a) Polymerization:
The polymer solution of Example 1 was used.
2b) Modification:
720 g of polymer solution from 1a) were transferred into a 2 L reactor. The solution was admixed with a solution of 0.13 g of disulphur dichloride in 10 mL of hexane at 65° C. for modification. The solution was stirred at 65° C. for a further 15 min. The polymer was precipitated by introduction into 5 kg of ethanol, stabilized with further Irganox 1520 (0.1 phr) and vacuum dried at 70° C.
Final Mooney viscosity (ML 1+4 at 100° C.): 35.9 MU, corresponds to K of equation (I).
Gel content<0.3 wt %
2c) Determination of Degree of Branching
A mixture of 4 g of DBD with 6 g of talcum and 0.08 g of iron phthalocyanine was mixed in a mortar by way of transformation mixture.

70 g of the polymer from 2b) were admixed with 0.44 g of the transformation mixture on a laboratory roll at 120° C. Roll nip was 0.4 mm, roll diameter was 10 cm. Rolling time was 15 min.
Mooney viscosity (ML 1+4 at 100° C.): 30.8 MU, corresponds to L of equation (I).
Degree of branching: 17%
Computed as per equation (I): degree of branching=(K−L)/L*100=(35.9−30.8)/30.8*100=17%

EXAMPLE 3: DETERMINING A 53% DEGREE OF BRANCHING IN A MODIFIED POLYMER OF HIGH MOONEY VISCOSITY

3a) Polymerization:
A dry, nitrogen-inertized 20 L steel autoclave was charged with 8500 g of hexane (dried over molecular sieve), 1300 g of 1,3-butadiene, 21 mmol of a 20% solution of diisobutylaluminium hydride in hexane, 1.44 mmol of a 10% solution of ethylaluminium sesquichloride in hexane, and also 1.44 mmol of a 40% solution of neodymium versatate in hexane. The autoclave contents were heated to 73° C. with stirring and polymerized for 60 min with stirring. The temperature in the reactor was increased to 90° C. The polymerization was stopped by admixture of 6.5 g of stearic acid (0.5 phr).

A conversion test sample was taken. Butadiene conversion after the polymerization was found to be 98.7%.
Original Mooney viscosity (ML 1+4 at 100° C.): 40 MU;
Microstructure: 97.5 wt % of 1,4-cis, 2.0 wt % of 1,4-trans, 0.5 wt % of 1,2-vinyl
3b) Modification:
The polymer solution was admixed with 3.33 g of disulphur dichloride (0.3 phr) at 95° C. for modification. The solution was stirred at 95° C. for a further 10 min. The polymer was precipitated by introduction into 5 kg of ethanol, stabilized with Irganox 1520 (0.2 phr) and vacuum dried at 70° C.

Final Mooney viscosity (ML 1+4 at 100° C.): 62.7 MU, corresponds to K of equation (I).
Gel content<0.3 wt %
3c) Determination of Degree of Branching A mixture of 4 g of DBD with 6 g of talcum and 0.08 g of iron phthalocyanine was mixed in a mortar by way of transformation mixture.

In a Brabender type internal mixer turning at 20 rpm, 230 g of rubber were mixed and heated to 130° C. in the course of 5 min. 1.44 g of transformation mixture from Example 1c) were added thereto and mixed in under the same conditions for 1 min.
Mooney viscosity (ML 1+4 at 100° C.): 41.0 MU, corresponds to L of equation (I)
Degree of branching: 53%
Computed as per equation (I): degree of branching=(K−L) L*100=(62.7−41)/41*100=53

COMPARATIVE EXAMPLE 4

To carry out these tests, 70 g of the modified polymer from Example 3b) were stored for 60 min in a drying cabinet at 145° C. without the addition of a transformation mixture. The polymer is found to remain stable.
Polymer before the treatment Mooney viscosity (ML 1+4 at 100° C.)=62.7 MU; MSR 0.46
Polymer after treatment: Mooney viscosity (ML 1+4 at 100° C.)=62.8 MU; MSR 0.46
→ no branching

COMPARATIVE EXAMPLE 5

These tests were carried out by rolling 200 g of the modified polymer from Example 3b) without the addition of a transformation mixture at 130° C. for 15 min in a roll nip of 0.5 mm and a roll diameter of 10 cm without further additions. The polymer is found to remain stable.
Polymer before the treatment: Mooney viscosity (ML 1+4 at 100° C.)=62.7 MU
Polymer after the treatment: Mooney viscosity (ML 1+4 at 100° C.)=62.0 MU
→ no branching

What is claimed is:
1. A process for determining the degree of branching of modified diene polymers modified from original diene polymers to increase the degree of crosslinking/branching thereof, and the Mooney viscosity of the original diene polymers is unknown, the process comprising:
 determining the Mooney viscosity (ML 1+4 at 100° C.) of the modified diene polymers,
 treating the modified diene polymers with a transformation mixture, thereby forming further modified diene polymers, wherein the transformation mixture comprises a compound of general formula (I)

$$R^1-S-S-R^1 \quad (I)$$

where
  $R^1$ in either occurrence is the same or different and is selected from a group consisting of
   moieties of formula (II)

$$C_6(R^2)_5-(C=O)-N(R^3)-C_6(R^2)_4- \quad (II)$$

where $R^2$ and $R^3$ in each occurrence is the same or different and each represent a hydrogen radical, a linear or branched alkyl radical of 1 to 16 carbon atoms, a phenyl radical, or a cycloalkyl radical of 5 to 8 carbon atoms;

moieties of formula (III)

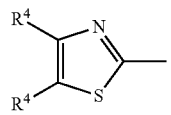

where $R^4$ in either occurrence is the same or different and represents a hydrogen, halogen, nitro or hydroxyl radical, a linear or branched alkyl radical of 1 to 12 carbon atoms, a linear or branched alkoxy radical of 1 to 12 carbon atoms, a phenyl radical, or a cycloalkyl radical of 5 to 8 carbon atoms, or the $R^4$'s combine to form the moiety of formula (IV);

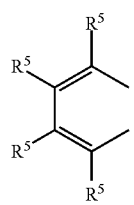

where $R^5$ in each occurrence is the same or different and represents a hydrogen or hydroxyl radical, a linear or branched alkyl radical of 1 to 12 carbon atoms, a linear or branched alkoxy radical of 1 to 12 carbon atoms, a phenyl radical, or a cycloalkyl radical of 5 to 8 carbon atoms;

moieties of formula (V)

$$(R^6O)_3Si-(CH_2)_n-(Y)_m- \quad (V)$$

where
   n is an integer from 1 to 12;
   m is from 0 to 4;
   $R^6$ in each occurrence is the same or different and represents a linear or branched alkyl radical of 1 to 16 carbon atoms, a phenyl radical or a cycloalkyl radical of 5 to 8 carbon atoms;
   Y represents sulphur, or a moiety of formula VIa, VIb, VIc, VId or VIe

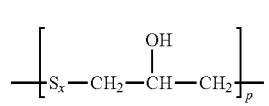

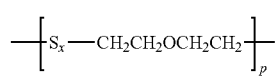

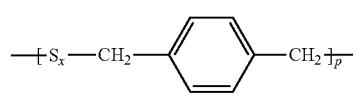

-continued

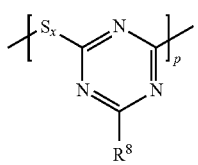

(VIe)

where
x' is an integer from 1 to 8;
p is an integer from 1 to 12;
$R^8$ in each occurrence is the same or different and represents a linear or branched alkyl radical of 1 to 16 carbon atoms, an alkoxy radical of 1 to 16 carbon atoms, a phenyl radical or a phenoxy radical;
moieties of formula (VII)

$(R^9)_2N—(C=Z)—$ (VII)

where
Z represents sulphur or oxygen,
$R^9$ in either occurrence is the same or different and represents a linear or branched alkyl radical of 1 to 16 carbon atoms, a phenyl radical or a cycloalkyl radical of 5 to 8 carbon atoms; or
moieties of formula (VIII)

$R^{10}—O—C(=S)—$ (VIII)

where
$R^{10}$ is the same or different and represents a linear or branched alkyl radical of 1 to 16 carbon atoms, a phenyl radical or a cycloalkyl radical of 5 to 8 carbon atoms,
determining the Mooney viscosity (ML 1+4 at 100° C.) of the further modified diene polymers, wherein the Mooney viscosity of the further modified diene polymers corresponds to the Mooney viscosity of the original diene polymers; and
calculating the degree of branching of the modified diene polymers relative to the original diene polymers to by equation (I) wherein:

degree of branching in %=$(K-L)/L*100$ where
K is the Mooney viscosity (ML 1+4 at 100° C.) of the modified diene polymers before treating with the transformation mixture, and
L is the Mooney viscosity (ML 1+4 at 100° C.) of the further modified diene polymers after treatment with the transformation mixture.

2. The process according to claim 1, wherein the transformation mixture comprises 2,2'-dibenzamidodiphenyl disulphide (DBD).

3. The process according to claim 1, wherein the transformation mixture comprises the compound of formula (IXa)

$(EtO)_3Si—C_3H_6—S_4—C_3H_6—Si(OEt)_3$ (IXa).

4. The process according to claim 1, wherein the transformation mixture comprises the compound of formula (IXb)

$(EtO)_3Si—C_3H_6—S_2—C_3H_6—Si(OEt)_3$ (IXb).

5. The process according to claim 1, wherein the transformation mixture comprises tetramethylthiuram disulphide.

6. The process according to claim 1, wherein the transformation mixture comprises transition metal salts, by way of activator, selected from the group consisting of Fe, Co, Cu, Ni, Mn, and Cr.

7. The process according to claim 6, wherein the Fe salts comprise Fe phthalocyanine or Fe hematoporphyrin.

8. The process according to claim 1, wherein the transformation mixture comprises, by way of activator, pentachlorothiophenol and salts thereof.

9. The process according to claim 1, wherein the transformation mixture further comprises an organic peroxide activator of formula (VIII)

$R^{11}—O—O—R^{12}$, (VIII)

where
$R^{11}$ and $R^{12}$ are the same or different and each represent
a
hydrogen radical,
a linear or branched alkyl radical of 1 to 16 carbon atoms, a phenyl radical or a cycloalkyl radical of 5 to 8 carbon atoms, or
a carboxyl radical $R^{13}—(C=O)—$, where $R^{13}$ represents a linear or branched alkyl radical of 1 to 16 carbon atoms, a phenyl radical or a cycloalkyl radical of 5 to 8 carbon atoms.

10. The process according to claim 1, wherein the transformation mixture further comprises waxes and/or fillers.

11. The process according to claim 1, wherein the treating step comprises mixing the modified diene polymer with the transformation mixture under thermal or mechanical input of energy.

12. The process according to claim 1, wherein the treating step comprises mixing the modified diene polymer with the transformation mixture in a mixer, in an extruder, or on a roll at a temperature of 70° C. to 160° C.

13. The process according to claim 1, wherein the transformation mixture is present in amounts of 0.01 to 2 wt %, based on 100 wt % of the modified diene polymer used.

14. The process according to claim 1, wherein the transformation mixture comprises:
a) 5 to 100 wt % of one or more compounds of formula (I),
b) optionally 0.01 to 5 wt % of activators, at the quantitative expense of compound of formula (I),
c) optionally 0.01 to 90 wt % of waxes, at the quantitative expense of compound of formula (I),
d) optionally 0.01 to 90 wt % of fillers, at the quantitative expense of compound of formula (I),
based on 100 wt % of transformation mixture.

15. The process according to claim 1, wherein the modified diene polymers are in the form of a solid material.

16. The process according to claim 1, wherein:
for the moieties of formula (II)
$R^2$ and $R^3$ in each occurrence is the same or different and each represent a hydrogen radical, a linear or branched alkyl radical of 1 to 8 carbon atoms, a phenyl radical, or a cycloalkyl radical of 5 to 8 carbon atoms;
for the moieties of formula (III)
$R^4$ in either occurrence is the same or different and represents a hydrogen, halogen, nitro or hydroxyl radical, a linear or branched alkyl radical of 1 to 8 carbon atoms, a linear or branched alkoxy radical of 1 to 8 carbon atoms, a phenyl radical, a cycloalkyl radical of 5 to 8 carbon atoms or the $R^4$'s combine to form the moiety of formula (IV); and $R^5$ in each occurrence is the same or different and represents a hydrogen or hydroxyl radical, a linear or branched alkyl radical of 1 to 8 carbon atoms, a linear or branched alkoxy radical of 1 to 8 carbon atoms, a phenyl radical, or a cycloalkyl radical of 5 to 8 carbon atoms;

for the moieties of formula (V)

n is an integer from 1 to 6;

m is from 0 to 2;

$R^6$ in each occurrence is the same or different and represents a linear or branched alkyl radical of 1 to 8 carbon atoms, a phenyl radical or a cycloalkyl radical of 5 to 8 carbon atoms;

x' is an integer from 2 to 6;

p is an integer from 1 to 6; and $R^6$ in each occurrence is the same or different and represents a linear or branched alkyl radical of 1 to 8 carbon atoms, an alkoxy radical of 1 to 8 carbon atoms, a phenyl radical or a phenoxy radical;

for the moieties of formula (VII)

$R^9$ in either occurrence is the same or different and represents a linear or branched alkyl radical of 1 to 8 carbon atoms, a phenyl radical or a cycloalkyl radical of 5 to 8 carbon atoms; and for the moieties of formula (VIII)

$R^{10}$ is the same or different and represents a linear or branched alkyl radical of 1 to 8 carbon atoms, a phenyl radical or a cycloalkyl radical of 5 to 8 carbon atoms.

17. The process according to claim 16, wherein the transformation mixture further comprises an organic peroxide activator of formula (VIII)

where $R^{11}$ and $R^{12}$ are the same or different and each represent
a hydrogen radical,
a linear or branched alkyl radical of 1 to 8 carbon atoms, a phenyl radical or a cycloalkyl radical of 5 to 8 carbon atoms, or
a carboxyl radical $R^{13}$—(C=O)—, where $R^{13}$ represents a linear or branched alkyl radical of 1 to 8 carbon atoms, a phenyl radical or a cycloalkyl radical of 5 to 8 carbon atoms.

18. The process according to claim 17, wherein the treating step comprises mixing the modified diene polymer with the transformation mixture at a temperature of 80° C. to 120° C.

* * * * *